United States Patent
Kunzler et al.

(10) Patent No.: US 6,703,378 B1
(45) Date of Patent: Mar. 9, 2004

(54) VITREORETINAL TAMPONADES BASED ON FLUOROSILICONE FLUIDS

(75) Inventors: Jay F. Kunzler, Canandaigua, NY (US); Richard M. Ozark, Solvay, NY (US); Joseph C. Salamone, Fairport, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 21 days.

(21) Appl. No.: 10/247,452

(22) Filed: Sep. 19, 2002

(51) Int. Cl.[7] .................... A61K 31/695; C07F 7/04
(52) U.S. Cl. .................... 514/63; 528/25; 528/37; 556/448

(58) Field of Search .............................. 556/448; 528/25, 528/37; 514/63

(56) References Cited

U.S. PATENT DOCUMENTS

| 5,480,573 A |   | 1/1996 | Durfee et al. ............. 252/78.3 |
| 5,548,054 A | * | 8/1996 | Okada et al. .................. 528/25 |
| 5,595,962 A |   | 1/1997 | Caporiccio et al. ......... 508/206 |
| 5,635,579 A |   | 6/1997 | Evans et al. .................. 528/37 |

* cited by examiner

*Primary Examiner*—Peter O'Sullivan
(74) *Attorney, Agent, or Firm*—Rita D. Vacca

(57) ABSTRACT

Fluorosilicone fluids useful as high-density fluid ocular tamponades and methods of producing, purifying and using the fluorosilicone fluids in an ocular surgical procedure for retinal treatment.

13 Claims, No Drawings

VITREORETINAL TAMPONADES BASED ON FLUOROSILICONE FLUIDS

FIELD OF THE INVENTION

The present invention relates to novel, fluorosilicone fluids, and more particularly, to fluorosilicone fluids useful as high-density fluid ocular tamponades, methods of producing the fluorosilicone fluids and methods of using the fluorosilicone fluids in vitreoretinal surgical procedures.

BACKGROUND OF THE INVENTION

Ocular tamponades are vitreous substitutes that are used to reposition the retina of an eye in instances where a reattachment is not achievable by natural healing or by laser coagulation. The purpose of a vitreous substitute is to provide long-term tamponade of the retina, i.e., exhibit an ideal tamponade pressure (force/area) to position and maintain the retina in place while not damaging the retina. The tamponade pressure is a function of the density of the tamponade polymer and the volume occupied thereby in the vitreous. The ideal tamponade is non-toxic, chemically inert and highly transparent. Current commercially used tamponades include perfluorocarbon-liquids, balanced salt solutions, silicone oil or fluid and gases, such as air, sulfur hexafluoride ($SF_6$) and perfluorocarbons (PFCs). The type of tamponade used depends on the severity of the retinal detachment. The addition of a PFC fluid that has a high specific gravity of approximately 1.7 to 2.0 g/cm$^3$ expulses the subretinal fluid into the vitreous cavity and pushes the retina into place. Such fluids reposition the detached retina very effectively, but can only be used for short-term application because with long term PFC fluid use, retinal necrosis occurs. This is believed to be due to a combination of the high solubility of oxygen in the PFC fluids and the high density of the PFC fluids. Silicone oil is the preferred tamponade in cases of severe detachment, where the tamponade will be used six months or longer. Silicone oil, however, has a density of less than 1 (0.98 g/cm$^3$) and is therefore only useful for retinal detachment of the superior portion of the eye. The silicone oil in the vitreous will migrate to the upper position of the vitreous only and is unacceptable in cases of lower retinal detachments or where there may be a risk of vitreoretinopathy in the lower position of the vitreous. Further, for the aphakic eye, the silicone oil will tend to move to the anterior chamber of the eye during sleep and come in contact with the corneal endothelium, creating a number of serious ocular defects.

Because of the noted shortcomings of current, commercially available ocular tamponades, there is a need for ocular tamponades that are relatively easy to synthesize and purify and that both the viscosity and density can be controlled.

SUMMARY OF THE INVENTION

The present invention is a novel high-density vitreoretinal fluid tamponade that is based on a fluorosilicone fluid. Preferred fluorosilicone fluids of the present invention have the general structure illustrated in Formula 1 below:

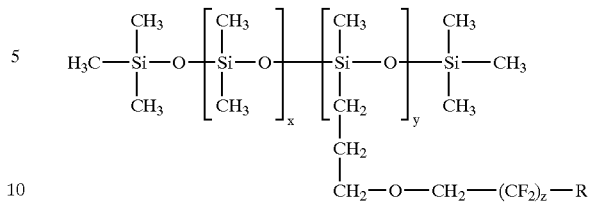

Formula 1 wherein x is an integer less than 500; y is an integer less than 500; x+y is equal to an integer greater than 1 and less than 1000; z is an integer less than 100; and R is selected from the group consisting of hydrogen and fluorine.

The high-density fluorosilicone fluid vitreoretinal tamponades of the present invention are relatively easy to synthesize and purify. Likewise, both the viscosity and density can be controlled through the respective degree of polymerization and degree of fluoro side-chain substitution.

Accordingly, it is an object of the present invention to provide a high-density vitreoretinal tamponade.

Another object of the present invention is to provide a process for the manufacture of a high-density vitreoretinal tamponade.

Another object of the present invention is to provide a process for using a high-density vitreoretinal tamponade in a surgical procedure.

Another object of the present invention is to provide a process for manufacturing vitreoretinal tamponades that allows for control of the density and viscosity of the vitreoretinal tamponade.

Still another object of the present invention is to provide a vitreoretinal tamponade suitable for relatively long term use in an eye.

A further object of the present invention is to provide a process for manufacturing and using a vitreoretinal tamponade suitable for relatively long term use in an eye.

These and other objectives and advantages of the present invention, some of which are specifically described and others that are not, will become apparent from the detailed description and claims that follow.

DETAILED DESCRIPTION OF THE INVENTION

The subject invention is a high-density vitreoretinal fluid tamponade based on a fluorosilicone fluid. The preferred fluorosilicone fluids of the present invention have the general structure illustrated in Formula 1 below:

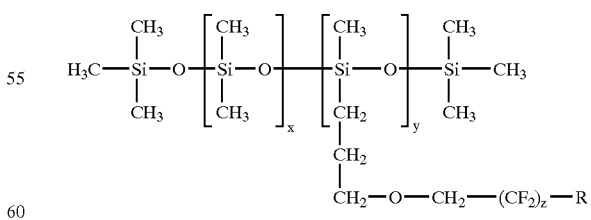

Formula 1 wherein x is an integer less than 500; y is an integer less than 500; x+y is equal to an integer greater than 1 and less than 1000; z is an integer less than 100; and R is selected from the group consisting of hydrogen and fluorine.

The high-density fluorosilicone fluid vitreoretinal tamponades of the present invention are relatively easy to synthesize and purify. Synthesis of the fluorosilicone fluid vitreoretinal tamponades of the present invention is accomplished by either a one-step ring opening polymerization process or a two-step ring opening/hydrosilation process as illustrated in Scheme 1 below.

Scheme 1

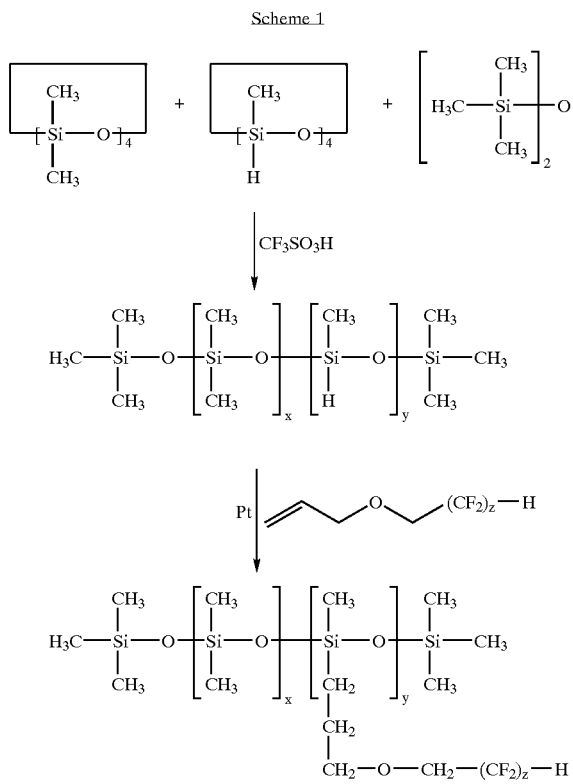

During synthesis of the subject fluorosilicone fluid, both viscosity and density can be controlled through the respective degree of polymerization and degree of fluoro side-chain substitution. For example, should increased density and/or viscosity be desired, the same is achieved by increasing the siloxane chain length and increasing the fluoro side-chain substitution. Likewise, should decreased density and/or viscosity be desired, the same is achieved by decreasing the siloxane chain length and decreasing the fluoro side-chain substitution.

Once synthesized, the subject fluorosilicone fluid is then purified by supercritical fluid extraction, solvent extraction or high vacuum devolatilization as known by those skilled in the art of purification.

The fluorosilicone fluid vitreoretinal tamponades of the present invention are described in still greater detail in the examples that follow. It should be noted that the procedure set forth in the following examples represents only one of many possible procedures useful in the preparation of the subject fluoro functionalized siloxanes.

EXAMPLE 1

Ring-opening/Hydrosilation Procedure

Synthesis of Trimethylsilyl-Capped Poly (25 mole % methyl siloxane)-co-(75 mole % dimethylsiloxane)($T_2D_{75}D_{25}H$)

To a 1000 mL round bottom flask under dry nitrogen was added octamethylcyclotetrasiloxane ($D_4$ (371.9 g, 1.25 mole)), tetramethylcyclotetrasiloxane ($D_4H$ (100.4 g, 0.42 mole)) and hexamethyldisiloxane ($T_2$ (0.7 mole)). Trifluoromethane sulfonic acid (0.25%, 1.25 g, 8.3 mmole) was added as initiator. The reaction mixture was stirred 24 hours with vigorous stirring at room temperature. Sodium bicarbonate (10 g, 0.119 mole) was then added and the reaction mixture was again stirred for 24 hours. The resultant solution was filtered through a $0.3\mu$ teflon® (E. I. DuPont de Nemours and Company, Wilmington, Del.) filter. The filtered solution was vacuum stripped and placed under vacuum (>0.1 mm Hg) at 50° C. to remove the unreacted silicone cyclics. The resulting silicone hydride functionalized siloxane was a viscous, clear fluid. (Yield 70%; SEC: Mn=7,500, Mw/Mn=2.2.)

EXAMPLE 2

General Procedure for the Synthesis of the Fluoro Side Chain Siloxanes

Synthesis of Methacrylate End-Capped Poly (25 mole% (3-(2,2,3,3,4,4,5,5-octafluoropentoxy)propyl methyl siloxane)-co-(75 mole% dimethylsiloxane) (Scheme 2)

To a 500 mL round bottom flask equipped with a magnetic stirrer and water condenser was added $T_2D_{75}D_{25}H$ (0.002 mole), allyloxyoctafluoropentane (27.2 g, 0.1 mole), tetramethyldisiloxane platinum complex (2.5 mL of a 10% solution in xylenes), 75 mL of dioxane and 150 mL of anhydrous tetrahydrofuran under a nitrogen blanket. The reaction mixture was heated to 75° C. and the reaction was monitored by IR and $^1$H-NMR spectroscopy for loss of silicone hydride. The reaction was complete in 4 to 5 hours of reflux. The resulting solution was placed on a rotoevaporator to remove tetrahydrofuran and dioxane. The resultant crude product was diluted with 300 mL of a 20% methylene chloride in pentane solution and passed through a 15 gram column of silica gel using a 50% solution of methylene chloride in pentane as eluant. The collected solution was again placed on the rotoevaporator to remove solvent and the resultant clear oil was placed under vacuum (>0.1 mm Hg) at 50° C. for four hours. The resulting octafluoro functionalized sidechain siloxane was a viscous, clear fluid. (Yield 65%; SEC: Mn=17535, Mw/Mn=1.7 (see attached table.))

The chemical properties of the fluorosilicone fluid vitreoretinal tamponades of the present invention are described in detail in Table 1 below.

TABLE 1

Chemical Properties of Perfluorosilicone Fluids for Retinal Tamponade Application

| Compound | Viscosity (cps) | Refractive Index (25° C.) | Density (g/cm³) | Surface Tension (mN/m) | Interfacial Tension (mN/m) |
|---|---|---|---|---|---|
| 1* | 9300 | 1.3914 | 1.115 | 25.5 | 30.4 |
| 2** | 2150 | 1.3837 | 1.254 | 27.1 | 31.9 |
| 3*** | 1120 | 1.3860 | 1.212 | 26.1 | 27.0 |
| 4**** | 130 | 1.3964 | 1.032 | 24.1 | 39.0 |
| 5***** | 185 | 1.3823 | 1.144 | 23.2 | 32.1 |
| 6****** | 980 | 1.3668 | 1.248 | 23.9 | 33.1 |
| 7******* | 9300 | 1.3860 | 1.124 | 27.2 | 31.8 |
| Commercial Silicone Oil | variable | 1.4040 | 0.962 | 24.2 | N.A. |

TABLE 1-continued

Chemical Properties of Perfluorosilicone
Fluids for Retinal Tamponade Application

| Compound | Viscosity (cps) | Refractive Index (25° C.) | Density (g/cm³) | Surface Tension (mN/m) | Interfacial Tension (mN/m) |
|---|---|---|---|---|---|
| Tamponade Material Requirements | 100–6000 | 1.30–1.40 | 1.0–1.6 | 20–30 | 25–50 |

*x = 75, y = 25, z = 4, R = H
**x = 13, y = 37, z = 4, R = H
***x = 25, y = 25, z = 4, R = H
****x = 45, y = 5, z = 4, R = H
*****x = 45, y = 5, z = 8, R = F
******x = 75, y = 25, z = 8, R = F
*******x = 100, y = 100, z = 8, R = F

Fluorosilicone fluid tamponades synthesized and purified using the processes of the present invention are used as customary in the field of ophthalmology. For example, in a surgical vitreoretinal procedure, the fluorosilicone fluid tamponade synthesized and purified in accordance with the processes of the present invention is placed and maintained in the posterior segment of the eye for the desired period of time prior to the removal thereof.

While there is shown and described herein a process for the synthesis and purification of fluorosilicone fluids for use as ocular tamponades, it will be manifest to those skilled in the art that various modifications may be made without departing from the spirit and scope of the underlying inventive concept and that the same is not limited to particular processes herein described except insofar as indicated by the scope of the appended claims.

We claim:

1. A fluorosilicone fluid vitreoretinal tamponade comprising:

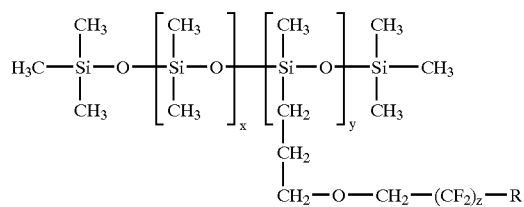

wherein x is an integer less than 500; y is an integer less than 500; x+y is equal to an integer greater than 1 and less than 1000; z is an integer less than 100; R is selected from the group consisting of hydrogen and fluorine; and wherein the viscosty is 100 cps or greater.

2. The tamponade of claim 1 whereby x is 75, y is 25, z is 4 and R is hydrogen.

3. The tamponade of claim 1 whereby x is 100, y is 100, z is 8 and R is fluorine.

4. A method of producing the tamponade of claim 1 comprising:

polymerizing fluoro-based monomers with siloxane monomers using a one-step ring opening process.

5. A method of producing the tamponade of claim 1 comprising:

polymerizing fluoro-based monomers with siloxane monomers using a two-step ring opening and hydrosilation process.

6. A method of purifying the tamponade of claim 1 comprising:

extracting said tamponade through supercritial fluid extraction or solvent extraction.

7. A method of purifying the tamponade of claim 1 comprising:

exposing said tamponade to high vacuum devolatilization process.

8. A method of using the tamponade of claim 1 in a surgical procedure comprising:

creating an incision into a posterior chamber of an eye;

positioning damaged retinal tissue within the eye; and filling said posterior chamber of the eye with said tamponade.

9. A method of using the tamponade of claim 1 in an ophthalmic surgical procedure comprising:

creating an incision into a posterior chamber of an eye; and filling said posterior chamber of the eye with said tamponade.

10. The tamponade of claim 1 whereby the density is 1.0 g/cm³ or greater.

11. The tamponade of claim 1 whereby the surface tension is 20 mN/m or greater.

12. The tamponade of claim 1 whereby the interfacial tension is 25 mN/m or greater.

13. The tamponade of claim 1 whereby the refractive index is 1.3 or greater at 25° C.

* * * * *